United States Patent [19]

Hoffman

[11] Patent Number: 4,645,969.
[45] Date of Patent: Feb. 24, 1987

[54] SKIN TANNING FLUORESCENT LAMP CONSTRUCTION UTILIZING A PHOSPHOR COMBINATION

[75] Inventor: Mary V. Hoffman, South Euclid, Ohio

[73] Assignee: General Electric Company, Schenectady, N.Y.

[21] Appl. No.: 174,623

[22] Filed: Aug. 1, 1980

[51] Int. Cl.$^4$ .......................... H01J 1/62; H01J 63/04
[52] U.S. Cl. ................................................. 313/487
[58] Field of Search ....................................... 313/487

[56] References Cited

U.S. PATENT DOCUMENTS

| | | | |
|---|---|---|---|
| 2,846,403 | 8/1958 | Hoekstra et al. | 252/301.6 |
| 3,431,215 | 3/1969 | Chenot | 252/301.4 |
| 4,095,113 | 6/1978 | Wolff | 250/494 |
| 4,150,321 | 4/1979 | Schetters et al. | 313/486 |
| 4,305,019 | 12/1981 | Graff et al. | 313/487 |

FOREIGN PATENT DOCUMENTS

| | | | |
|---|---|---|---|
| 48-21626 | 6/1973 | Japan | 313/487 |
| 50-8860 | 4/1975 | Japan | 313/487 |

Primary Examiner—William L. Sikes
Assistant Examiner—Robert E. Wise
Attorney, Agent, or Firm—J. F. McDevitt; Philip L. Schlamp; Fred Jacob

[57] ABSTRACT

A skin tanning lamp construction of a fluorescent type utilizing a combination of two different phosphors to provide efficient artificial skin tanning along with improved color rendition. The particular phosphor combination can be utilized as a blended mixture having a sufficient level of a phosphor constituent to impart some visible radiation in the red color region to the composite lamp emission.

10 Claims, 1 Drawing Figure

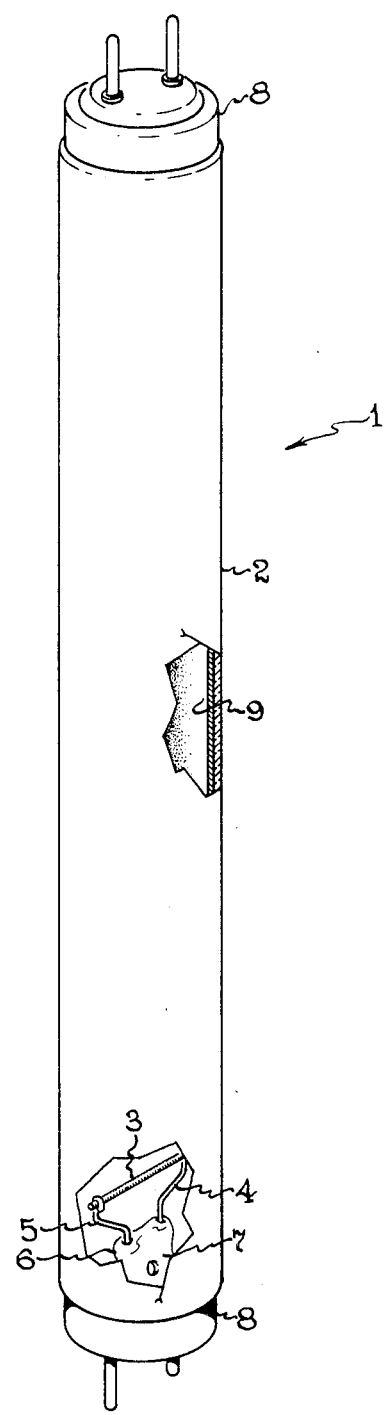

SKIN TANNING FLUORESCENT LAMP CONSTRUCTION UTILIZING A PHOSPHOR COMBINATION

BACKGROUND OF THE INVENTION

This invention relates generally to an improved low pressure mercury vapor discharge lamp of the fluorescent type having a particular type phosphor coating to emit skin tanning radiation when excited by ultraviolet radiation generated from the mercury vapor discharge. More particularly, the present type lamp construction provides satisfactory skin tanning with radiation in the UVA spectral region (320–400 nanometers wavelength) and which may further desirably include a phosphor combination providing preselected amounts of radiation in the UVB spectral region (280–320 nanometers wavelength) for additional skin tanning benefit.

Lamps of the fluorescent type to produce artificial skin tanning have been known for some time. The early lamps of this type utilized a coating of a single phosphor material to emit ultraviolet radiation in the approximate wavelength region 320–400 nanometers which produced artificial skin tanning without occasioning skin reddening (erythema) to any significant degree. A more recently introduced fluorescent lamp of this type generates both UVA and UVB radiation to promote more effective artificial skin tanning without further occasioning undesirable erythemal effects. Said improved fluorescent lamp of this type is described in U.S. patent application No. 72,958, filed Sept. 6, 1979, and assigned to the present assignee wherein the desired objective is achieved with a phosphor combination of a first phosphor emitting in the 320–400 nanometer region of the spectrum with a second phosphor emitting in the 280–320 nanometer region in the spectrum and which can be utilized as a blended mixture. A preferred phosphor material efficiently generating the desired UVB radiation is a lead-activated barium zinc silicate phosphor such as $BaZn_2Si_2O_7:Pb$ which is disclosed in U.S. Pat. No. 2,846,403, issued to Hoekstra and Clasens. A suitable phosphor material efficiently generating UVA radiation can be europium-activated strontium borate such as disclosed in U.S. Pat. No. 3,431,215.

All of the above type skin tanning fluorescent lamps produce blue color visible emission, however, attributable to strong mercury discharge lines in the visible region at wavelengths of approximately 405, 436, 546 and 578 nanometers wavelength. Such blue color lamp emission is objectionable from the standpoint of color rendition to the lamp users. Thus, skin tones as well as clothing worn by a person while exposed to the lamp emission have an unflattering appearance which is undesirable. It would thereby be of benefit to modify the lamp color emission in a manner to improve the color rendition and especially without significant loss of the skin tanning effect otherwise produced with a conventional lamp. It would also be desirable to improve the color rendition of said skin tanning fluorescent lamps without requiring structural modification in the lamp design or additional modification to the apparatus now employing the conventional lamps.

SUMMARY OF THE INVENTION

It has now been discovered that a particular combination of two different phosphor materials provides improved color rendition by a skin tanning type fluorescent lamp. More particularly, it has been found that a phosphor combination including a first phosphor which converts at least a portion of the mercury discharge radiation to skin tanning radiation with a second phosphor to produce visible radiation in the red color region of the visible spectrum provides better color rendition by the composite lamp emission. The improved phosphor combination can most simply be provided as a blended mixture in the form of a coating applied to the inner wall of the tubular lamp envelope. Accordingly, the presently improved skin tanning fluorescent lamp construction utilizes a sealed transparent envelope enclosing means to generate a low pressure mercury discharge within said envelope, and a coating contained within said envelope for conversion of at least a portion of the radiation emitted from said discharge to skin tanning radiation, wherein the improvement is a coating comprising a phosphor combination including a first phosphor which converts said radiation to skin tanning radiation and a second phosphor to produce visible radiation in the red color region of the visible spectrum for better color rendition by the composite lamp emission.

The first phosphor constituent in the present phosphor combination can be either a single phosphor material or a blended mixture of two or more individual phosphor materials. It is thereby contemplated to employ europium-activated strontium borate as said first phosphor constituent either alone or in combination, such as a blended mixture, with a suitable phosphor material generating UVB radiation to provide improved skin tanning effect. As previously indicated, a suitable UVB phosphor can be a lead-activated barium zinc silicate phosphor to be utilized at weight proportions in said blended mixture as disclosed in the aforementioned pending U.S. patent application No. 72,958. Still other phosphor materials such as cerium-activated strontium aluminate or barium silicate:Pb have been utilized as said first phosphor constituent in skin tanning type fluorescent lamps to convert the mercury discharge radiation to skin tanning radiation in the desired spectral region.

The second phosphor constituent in the present phosphor combination produces visible radiation in the red color region, as previously indicated, and can be selected either from a phosphor material which produces visible radiation primarily in the red color region of the visible spectrum or from a phosphor material which emits broader color emission to include significant red color emission. For example, conventional calcium halophosphate phosphor coactivated with antimony and manganese and which provides warm white color emission has been found suitable as the second phosphor constituent in the present phosphor combination. Trivalent europium-activated yttrium oxide phosphor provides an efficient source of red color emission in the present phosphor combination. Incorporation of a small but effective amount up to approximately 10 weight percent of the second phosphor constituent in the blended mixture has been found to impart effective color rendition to the composite lamp emission.

In one preferred embodiment, a blended mixture of lead-activated barium zinc silicate phosphor with divalent europium-activated strontium borate phosphor and trivalent europium-activated yttrium oxide phosphor in weight proportions as above generally specified provide improved color rendition with minimum of loss in skin tanning effectiveness. Another preferred embodiment utilizing a blended mixture of divalent europium-activated strontium borate phosphor with calcium halophosphate phosphor coactivated with antimony and manganese exhibiting a warm white color point also imparts improved color rendition with no greater loss in skin tanning effect. A third preferred embodiment imparting improved color rendition with minimal loss in skin tanning effect is provided with a blended mixture of lead-activated barium zinc silicate phosphor, divalent europium-activated strontium borate phosphor, and manganese-activated magnesium germanate.

BRIEF DESCRIPTION OF THE DRAWING

The accompanying drawing is a perspective view partially broken away of a fluorescent lamp construction in accordance with the present invention.

DESCRIPTION OF THE PREFERRED EMBODIMENTS

Referring to the accompanying drawing, there is shown a fluorescent lamp 1 comprising an elongated soda-lime silicate glass bulb 2 with circular cross section. The discharge assembly in said lamp is the usual electrode structure 3 at each end supported by inlead wires 4 and 5 which extend to a glass seal 6 in a stem mount 7 to the contacts of a base 8 affixed at opposite ends of the lamp. The discharge sustaining filling in the sealed glass tube is an inert gas such as argon or a mixture of argon and other gases at a low pressure in combination with a small quantity of mercury to provide the low vapor pressure manner of lamp operation. The inner surface of the glass bulb is provided with a phosphor coating 9 which is applied extending substantially the full length of the bulb and around the bulb circumferential inner wall.

To better illustrate the improvement obtained in emission behavior for the above type lamp construction utilizing the present lamp phosphor combination as a blended mixture, various conventional F40T12 lamps were constructed for operation at the conventional wattage input of electrical energy. Said lamps were coated in the conventional manner with a blend of the individual phosphor constituents identified in Table I below for a comparison of the relative skin tanning effect produced as well as the relative amount of red color emission being obtained from the lamps. Total lumen measurements were made for these test lamps by spectrophotometer. The percent red lumen measurements were made by transmitting the lamp light output through a CS2-62 filter having an absorption edge at 600 nanometer wavelength. The relative ultraviolet radiation values reported in said Table were derived by first measuring the ultraviolet radiation output from the test lamps with a photocell detector provided with optical filters responsive only to UVA or UVB regions of the spectrum. The relative values were then calculated with the output measurements obtained upon the first phosphor constituents alone representing 100%. The percentages reported upon the phosphor blends containing both first and second phosphor constituents represent the percentage fraction between said output measurements when compared with the output measurements for test lamps utilizing only the first phosphor constituents.

TABLE I

| SAMPLE | PHOSPHOR BLEND | | VISIBLE RADIATION | | RELATIVE ULTRAVIOLET RADIATION (Percent) | |
|---|---|---|---|---|---|---|
| | FIRST PHOSPHOR (Weight Percent) | SECOND PHOSPHOR (Weight Percent) | TOTAL LUMENS | % RED LUMENS | UVA REGION | UVB REGION |
| 1 | 8% BaZn$_2$SiO$_7$:Pb 92% SrB$_4$O$_7$:Eu | 0 | 190 | 1.3 | 100 | 100 |
| 2 | 7.8% BaZn$_2$SiO$_7$:Pb 90.2% SrB$_4$O$_7$:Eu | 2% Y$_2$O$_3$:Eu | 265 | 9.8 | 94 | 94 |
| 3 | 7.7% BaZn$_2$SiO$_7$:Pb 88.3% SrB$_4$O$_7$:Eu | 4% Y$_2$O$_3$:Eu | 303 | 15.9 | 94 | 93 |
| 4 | 7.5% BaZn$_2$SiO$_7$:Pb 86.5% SrB$_4$O$_7$:Eu | 6% Y$_2$O$_3$:Eu | 346 | 20.2 | 95 | 98 |
| 5 | 7.3% BaZn$_2$SiO$_7$:Pb 83.7% SrB$_4$O$_7$:Eu | 9% Y$_2$O$_3$:Eu | 404 | 25.2 | 90 | 93 |
| 6 | SrB$_4$O$_7$:Eu | 0 | 190 | 1.3 | 100 | 100 |
| 7 | 97% SrB$_4$O$_7$:Eu | 3% CaHalo | — | — | 93 | 93 |
| 8 | 94% SrB$_4$O$_7$:Eu | 6% CaHalo | — | — | 96 | 89 |
| 9 | 90% SrB$_4$O$_7$:Eu | 10% CaHalo | 370 | 7.2 | 96 | 93 |
| 10 | 8% BaZn$_2$SiO$_7$:Pb 92% SrB$_4$O$_7$:Eu | 0 | — | — | 100 | 100 |
| 11 | 7.8% BaZn$_2$SiO$_7$:Pb 90.2% SrB$_4$O$_7$:Eu | 2% Mg$_4$GeO$_6$:Mn$^{+4}$ | — | — | 92 | 104 |
| 12 | 7.6% BaZn$_2$SiO$_7$:Pb 87.4% SrB$_4$O$_7$:Eu | 5% Mg$_4$GeO$_6$:Mn$^{+4}$ | — | — | 87 | 99 |
| 13 | 7.2% BaZn$_2$SiO$_7$:Pb 82.8% SrB$_4$O$_7$:Eu | 10% Mg$_4$GeO$_6$:Mn$^{+4}$ | — | — | 84 | 90 |

From the total lumen values reported in the above Table, it can be noted that addition of a second phosphor constituent in the present phosphor combination increases the total output from the lamp generally proportional to the amount added. It can further be noted from the increase in percent of red lumens reported in said Table with increase of the second phosphor constituent in the present phosphor combination that color rendition is also improved thereby. The percentage increase in red lumens for lamp samples 1-5 is also shown as greater than for said increase in lamp samples 6-9. The basis for this difference is believed to be utilization of a highly efficient europium-activated yttrium oxide phosphor which has a narrow band emission at approximately 611 wavelength in the former lamps as compared with utilization of calcium halophosphate coactivated with antimony and manganese exhibiting a broader emission peak at approximately 580 nanometers wavelength in the latter lamps.

While the relative ultraviolet radiation values reported in the above Table do confirm some loss in skin tanning effect attributable to incorporation of said second phosphor constituent in the present phosphor combination, such reduction does not prevent efficient artificial skin tanning. At most, it would be expected from the reported values that possibly 5–10 percent additional exposure time is required to obtain an equal tanning effect with the present lamps. A comparison between the phosphor combinations illustrated in said Table with respect to skin tanning effect finds the calcium halophosphate phosphor mixture to experience the least amount of loss in the UVA region for the most part. Lamp samples 11–13, utilizing manganese-activated magnesium germanate phosphor as the second phosphor constituent, exhibit least loss in the UVB spectral region which is desirable. The UVB radiation is recognized as beneficial in promoting formation of melanin pigment which is said to initiate the tanning process. On the other hand, lamp samples 2–5, utilizing europium-activated yttrium oxide phosphor as the second phosphor constituent, exhibit less aggregate loss in both UVA and UVB spectral regions. Such result possibly signifies the most effective combination in producing efficient artificial skin tanning accompanied by improved skin tone and fabric color rendition.

From the above preferred embodiments, it is evident that a particular two-component phosphor combination has been provided which achieves effective artificial skin tanning with improved color rendition from the composite lamp emission. It will also be apparent, however, that modifications are contemplated in the illustrated embodiment through substitution of the individual phosphor constituents as well as by compositional variation of the individual phosphor constituents selected without departing from the true spirit and scope of this invention. Consequently, it is intended to limit the present invention only by the scope of the following claims.

What I claim as new and desire to secure by U.S. Letters Patent is:

1. An improved skin tanning fluorescent lamp having a sealed transparent envelope enclosing means to generate a low pressure mercury discharge within said envelope, and a coating contained within said envelope for conversion of at least a portion of the radiation emitted from said discharge to skin tanning radiation, the improved coating comprising a phosphor combination including a first phosphor which converts said radiation to skin tanning radiation in the 320–400 nanometer spectral region and a second phosphor to produce visible radiation in the red color region of the visible spectrum for better color rendition by the composite lamp emission.

2. An improved lamp as in claim 1 wherein the phosphor combination is a blended mixture.

3. An improved lamp as in claim 2 wherein the second phosphor proportion in said mixture is present from a small but effective amount up to approximately 10 weight percent.

4. An improved lamp as in claim 2 having a phosphor emitting in the 320–400 nanometer region of the spectrum blended with another phosphor emitting in the 280–330 nanometer region of the spectrum.

5. An improved lamp as in claim 4 wherein the second phosphor produces visible radiation primarily in the red color region of the visible spectrum.

6. An improved lamp as in claim 1 wherein the first phosphor is a blended mixture.

7. An improved lamp as in claim 1 wherein the second phosphor produces visible radiation primarily in the red color region of the visible spectrum.

8. An improved lamp as in claim 1 wherein the second phosphor produces visible broad bandwidth radiation of a warm white color to include significant red color emission.

9. An improved lamp as in claim 1 wherein the first phosphor emits in the 320–400 nanometer region of the spectrum and the second phosphor produces visible broad bandwidth radiation of a white color to include significant red color emission.

10. An improved lamp as in claim 1 having a blended mixture of lead-activated barium zinc silicate phosphor with divalent europium-activated strontium borate phosphor and trivalent europium-activated yttrium oxide phosphor.

* * * * *